US010052221B2

(12) United States Patent
Albertsson et al.

(10) Patent No.: US 10,052,221 B2
(45) Date of Patent: Aug. 21, 2018

(54) ORTHOPEDIC DEVICE FOR TREATING OSTEOARTHRITIS OF THE KNEE

(71) Applicant: Ossur Iceland ehf, Reykjavik (IS)

(72) Inventors: Halldor Albertsson, Aalborg Ost (DK); Arni Thor Ingimundarson, Gardabaer (IS); Helga Run Palsdottir, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 443 days.

(21) Appl. No.: 14/989,528

(22) Filed: Jan. 6, 2016

(65) Prior Publication Data

US 2016/0193066 A1    Jul. 7, 2016

Related U.S. Application Data

(60) Provisional application No. 62/100,319, filed on Jan. 6, 2015.

(51) Int. Cl.
*A61F 5/01* (2006.01)
(52) U.S. Cl.
CPC .......... *A61F 5/0125* (2013.01); *A61F 5/0109* (2013.01); *A61F 2005/0169* (2013.01); *A61F 2005/0172* (2013.01)
(58) Field of Classification Search
CPC ........ A61F 5/01; A61F 5/0123; A61F 5/0125; A61F 5/0109; A61F 2005/0169; A61F 2005/0172
USPC .......................................................... 602/16
See application file for complete search history.

(56) References Cited

U.S. PATENT DOCUMENTS

| | | | |
|---|---|---|---|
| 667,768 A | 2/1901 | Puy |
| 777,585 A | 12/1904 | Beatty |
| 937,478 A | 10/1909 | Sims |
| 1,153,334 A | 9/1915 | Oswald |
| 1,227,700 A | 5/1917 | Tucker |
| 1,328,541 A | 1/1920 | Palmer |

(Continued)

FOREIGN PATENT DOCUMENTS

| | | |
|---|---|---|
| CN | 101128169 A | 2/2008 |
| DE | 846 895 C | 8/1952 |

(Continued)

OTHER PUBLICATIONS

Article: "An Orthosis for Medial or Lateral Stabilization of Arthritic Knees", by S. Cousins and James Foort, Orthotics and Prosthetics, vol. 29, No. 4, pp. 21-26, Dec. 1975.

(Continued)

*Primary Examiner* — Tarla Patel
(74) *Attorney, Agent, or Firm* — Workman Nydegger (57) ABSTRACT

An orthopedic device includes a first panel defining opposed first and second sides. A second panel has a first end secured to the first side of the first panel along a seam between upper and lower corners of the seam, and a second end defining at least one flap securable to the second side of the first panel at a location site. A first strap has a first end secured to the first side of the first panel and extends from an upper portion of the seam including the upper corner of the seam and overlies at least a portion of the second panel. A dynamic force strap helically extends between upper and lower portions of the orthopedic device and connects to the first panel.

17 Claims, 5 Drawing Sheets

(56) References Cited

U.S. PATENT DOCUMENTS

| | | |
|---|---|---|
| 1,510,408 A | 9/1924 | Lychou |
| 1,622,211 A | 3/1927 | Sheehan |
| 2,032,923 A | 3/1936 | Eldridge |
| 2,179,903 A | 11/1939 | Spears |
| 2,467,907 A | 4/1949 | Peckham |
| 2,573,866 A | 11/1951 | Murphy |
| 2,717,841 A | 9/1955 | Biefeld et al. |
| 2,935,065 A | 5/1960 | Homier et al. |
| 3,031,730 A | 5/1962 | Morin |
| 3,046,981 A | 7/1962 | Biggs, Jr. et al. |
| 3,089,486 A | 5/1963 | Pike |
| 3,266,113 A | 8/1966 | Flanagan, Jr. |
| 3,463,147 A | 8/1969 | Stubbs |
| 3,514,313 A | 5/1970 | Martel et al. |
| 3,520,765 A | 7/1970 | Bateman |
| 3,528,412 A | 9/1970 | McDavid |
| 3,581,741 A | 1/1971 | Rosman |
| 3,561,436 A | 2/1971 | Gaylord, Jr. |
| 3,594,863 A | 7/1971 | Erb |
| 3,594,865 A | 7/1971 | Erb |
| 3,742,557 A | 7/1973 | Francois |
| 3,752,619 A | 8/1973 | Menzin et al. |
| 3,758,657 A | 9/1973 | Menzin et al. |
| 3,789,842 A | 2/1974 | Froimson |
| 3,804,084 A | 4/1974 | Lehman |
| 3,817,244 A | 6/1974 | Taylor |
| 3,851,357 A | 12/1974 | Ribich et al. |
| 3,877,426 A | 4/1975 | Nirschl |
| 3,916,077 A | 10/1975 | Damrau |
| 3,927,881 A | 12/1975 | Lemelson et al. |
| 3,945,046 A | 3/1976 | Stromgren |
| 3,955,565 A | 5/1976 | Johnson, Jr. |
| 4,193,395 A | 3/1980 | Gruber |
| 4,204,532 A | 5/1980 | Lind et al. |
| 4,240,414 A | 12/1980 | Theisler |
| 4,269,179 A | 5/1981 | Burton et al. |
| 4,269,181 A | 5/1981 | Delannoy |
| 4,275,716 A | 6/1981 | Scott, Jr. |
| 4,280,489 A | 7/1981 | Johnson, Jr. |
| 4,291,072 A | 9/1981 | Barrett et al. |
| 4,296,744 A | 10/1981 | Palumbo |
| 4,304,560 A | 12/1981 | Greenwood |
| 4,336,279 A | 6/1982 | Metzger |
| 4,372,298 A | 2/1983 | Lerman |
| 4,381,768 A | 5/1983 | Erichsen et al. |
| 4,386,723 A | 6/1983 | Mule |
| 4,396,012 A | 8/1983 | Cobiski |
| 4,470,857 A | 9/1984 | Casalou |
| 4,472,461 A | 9/1984 | Johnson |
| 4,506,661 A | 3/1985 | Foster |
| 4,528,440 A | 7/1985 | Ishihara |
| 4,554,913 A | 11/1985 | Womack et al. |
| 4,572,170 A | 2/1986 | Cronk et al. |
| 4,617,214 A | 10/1986 | Billarant |
| 4,632,098 A | 12/1986 | Grundei et al. |
| 4,677,713 A | 7/1987 | Copp |
| 4,693,921 A | 9/1987 | Billarant et al. |
| D292,529 S | 10/1987 | Saare |
| 4,697,583 A | 10/1987 | Mason et al. |
| 4,724,831 A | 2/1988 | Huntjens |
| 4,768,500 A | 9/1988 | Mason et al. |
| 4,775,310 A | 10/1988 | Fischer |
| D298,568 S | 11/1988 | Womack et al. |
| 4,782,605 A | 11/1988 | Cahpnick |
| 4,791,916 A | 12/1988 | Paez |
| 4,794,028 A | 12/1988 | Fischer |
| 4,801,138 A | 1/1989 | Airy et al. |
| 4,802,939 A | 2/1989 | Billarant et al. |
| 4,805,606 A | 2/1989 | McDavid, III |
| 4,854,308 A | 8/1989 | Drillio |
| 4,856,501 A | 8/1989 | Castillo et al. |
| 4,856,502 A | 8/1989 | Ersfeld et al. |
| 4,872,243 A | 10/1989 | Fischer |
| 4,922,929 A | 5/1990 | DeJournett |
| 4,933,035 A | 6/1990 | Billarant et al. |
| 4,953,543 A | 9/1990 | Grim et al. |
| 4,961,544 A | 10/1990 | Bidoia |
| 4,966,133 A | 10/1990 | Kausek |
| 4,989,593 A | 2/1991 | Campagna et al. |
| 4,991,574 A | 2/1991 | Pocknell |
| 4,991,640 A | 2/1991 | Verkindt et al. |
| 5,002,045 A | 3/1991 | Spademan |
| 5,005,527 A | 4/1991 | Hatfield |
| 5,016,621 A | 5/1991 | Bender |
| 5,018,514 A | 5/1991 | Grood et al. |
| 5,020,196 A | 6/1991 | Panach et al. |
| 5,022,109 A | 6/1991 | Pekar |
| 5,063,916 A | 11/1991 | France et al. |
| 5,067,772 A | 11/1991 | Koa |
| 5,077,870 A | 1/1992 | Melbye et al. |
| 5,085,210 A | 2/1992 | Smith, III |
| 5,112,296 A | 5/1992 | Beard et al. |
| 5,152,038 A | 10/1992 | Schoch |
| 5,154,682 A | 10/1992 | Kellerman |
| 5,157,813 A | 10/1992 | Carroll |
| 5,181,331 A | 1/1993 | Berger |
| 5,227,698 A | 7/1993 | Simpson et al. |
| 5,242,379 A | 9/1993 | Harris et al. |
| 5,267,951 A | 12/1993 | Ishii |
| 5,277,697 A | 1/1994 | France et al. |
| 5,277,698 A | 1/1994 | Taylor |
| 5,288,287 A | 2/1994 | Castillo et al. |
| 5,302,169 A | 4/1994 | Taylor |
| 5,314,455 A | 5/1994 | Johnson, Jr. et al. |
| 5,316,547 A | 5/1994 | Gildersleeve |
| 5,322,729 A | 6/1994 | Heeter et al. |
| 5,334,135 A | 8/1994 | Grim et al. |
| 5,344,135 A | 9/1994 | Isobe et al. |
| 5,368,549 A | 11/1994 | McVicker |
| 5,383,845 A | 1/1995 | Nebolon |
| 5,397,296 A | 3/1995 | Sydor et al. |
| 5,415,625 A | 5/1995 | Cassford |
| 5,431,623 A | 7/1995 | Rice |
| 5,437,619 A | 8/1995 | Malewicz et al. |
| 5,445,602 A | 8/1995 | Grim et al. |
| 5,449,341 A | 9/1995 | Harris |
| 5,458,565 A | 10/1995 | Tillinghast, III |
| 5,468,219 A | 11/1995 | Crippen |
| 5,472,413 A | 12/1995 | Detty |
| 5,474,524 A | 12/1995 | Carey |
| 5,497,513 A | 3/1996 | Arabeyre et al. |
| 5,500,268 A | 3/1996 | Billarant |
| 5,512,039 A | 4/1996 | White |
| 5,513,658 A | 5/1996 | Goseki |
| 5,514,081 A | 5/1996 | Mann |
| 5,527,269 A | 6/1996 | Reithofer |
| 5,540,982 A | 7/1996 | Scholz et al. |
| 5,542,911 A | 8/1996 | Cassford et al. |
| 5,562,605 A | 10/1996 | Taylor |
| 5,599,288 A | 2/1997 | Shirley et al. |
| 5,695,452 A | 2/1997 | Grim et al. |
| 5,614,045 A | 3/1997 | Billarant |
| 5,635,201 A | 6/1997 | Fabo |
| 5,638,588 A | 6/1997 | Jungkind |
| 5,654,070 A | 8/1997 | Billarant |
| 5,656,226 A | 8/1997 | McVicker |
| 5,665,449 A | 9/1997 | Billarant |
| 5,681,271 A | 10/1997 | Nelson |
| 5,685,830 A | 11/1997 | Bonutti |
| 5,713,837 A | 2/1998 | Grim et al. |
| D392,877 S | 3/1998 | Eguchi |
| 5,737,854 A | 4/1998 | Sussmann |
| 5,759,167 A | 6/1998 | Shields, Jr. et al. |
| 5,769,808 A | 6/1998 | Matthijs et al. |
| 5,774,902 A | 7/1998 | Gehse |
| 5,795,640 A | 8/1998 | Billarant |
| 5,807,294 A | 9/1998 | Cawley et al. |
| 5,823,981 A | 10/1998 | Grim et al. |
| 5,840,398 A | 11/1998 | Billarant |
| 5,857,988 A | 1/1999 | Shirley |
| 5,857,989 A | 1/1999 | Smith, III |
| 5,865,776 A | 2/1999 | Springs |
| 5,865,777 A | 2/1999 | Detty |
| 5,865,782 A | 2/1999 | Fareed |

(56) References Cited

U.S. PATENT DOCUMENTS

| | | |
|---|---|---|
| 5,873,848 A | 2/1999 | Fulkerson |
| 5,891,061 A | 4/1999 | Kaiser |
| 5,900,303 A | 5/1999 | Billarant |
| 5,916,187 A | 6/1999 | Brill |
| 5,948,707 A | 9/1999 | Crawley et al. |
| 5,971,946 A | 10/1999 | Quinn |
| 6,010,474 A | 1/2000 | Wycoki |
| 6,021,780 A | 2/2000 | Darby |
| 6,022,617 A | 2/2000 | Calkins |
| 6,024,712 A | 2/2000 | Iglesiasa et al. |
| 6,063,048 A | 5/2000 | Bodenschatz et al. |
| 6,110,138 A | 8/2000 | Shirley |
| 6,111,138 A | 8/2000 | Van Wijck et al. |
| 6,142,965 A | 11/2000 | Mathewson |
| 6,152,893 A | 11/2000 | Pigg et al. |
| 6,159,583 A | 12/2000 | Calkins |
| 6,250,651 B1 | 6/2001 | Reuss et al. |
| 6,254,554 B1 | 7/2001 | Turtzo |
| 6,267,741 B1 | 7/2001 | Lerman |
| RE37,338 E | 8/2001 | McVicker |
| 6,287,268 B1 | 9/2001 | Gilmour |
| 6,289,558 B1 | 9/2001 | Hammerslag |
| 6,360,404 B1 | 3/2002 | Mudge et al. |
| 6,368,295 B1 | 4/2002 | Lerman |
| 6,402,713 B1 | 6/2002 | Doyle |
| 6,405,731 B1 | 6/2002 | Ching |
| 6,413,232 B1 | 7/2002 | Townsend et al. |
| 6,416,074 B1 | 7/2002 | Maravetz et al. |
| 6,461,318 B2 | 10/2002 | Freeman et al. |
| 6,485,776 B2 | 11/2002 | Janusson et al. |
| 6,520,926 B2 | 2/2003 | Hall |
| 6,540,703 B1 | 4/2003 | Lerman |
| 6,540,709 B1 | 4/2003 | Smits |
| D477,409 S | 7/2003 | Mills et al. |
| 6,592,538 B1 | 7/2003 | Hotchkiss et al. |
| 6,592,539 B1 | 7/2003 | Einarsson et al. |
| 6,596,371 B1 | 7/2003 | Billarant et al. |
| 6,598,250 B1 | 7/2003 | Pekar |
| 6,543,158 B2 | 8/2003 | Dieckhaus |
| 6,656,142 B1 | 12/2003 | Lee |
| 6,666,894 B2 | 12/2003 | Perkins et al. |
| 6,689,080 B2 | 2/2004 | Castillo |
| 6,726,641 B2 | 4/2004 | Chiang et al. |
| 6,735,819 B2 | 5/2004 | Iverson et al. |
| 6,769,155 B2 | 8/2004 | Hess et al. |
| 6,773,411 B1 | 8/2004 | Alvarez |
| 6,861,371 B2 | 3/2005 | Kamikawa et al. |
| 6,861,379 B1 | 3/2005 | Blaszcykiewicz |
| 6,898,804 B2 | 5/2005 | Sandler |
| 6,898,826 B2 | 5/2005 | Draper et al. |
| 6,936,020 B2 | 8/2005 | Davis |
| D519,637 S | 4/2006 | Nordt et al. |
| D519,638 S | 4/2006 | Nordt et al. |
| 7,025,738 B2 | 4/2006 | Hall |
| D520,141 S | 5/2006 | Nordt et al. |
| D521,644 S | 5/2006 | Nordt et al. |
| 7,037,287 B2 | 5/2006 | Cormier et al. |
| 7,150,721 B2 | 12/2006 | Houser |
| 7,161,056 B2 | 1/2007 | Gudnason et al. |
| 7,169,720 B2 | 1/2007 | Etchells et al. |
| 7,198,610 B2 | 4/2007 | Ingimundarson et al. |
| 7,303,539 B2 | 12/2007 | Binder et al. |
| 7,367,958 B2 | 5/2008 | McBean et al. |
| 7,448,115 B2 | 11/2008 | Howell et al. |
| 7,597,675 B2 | 10/2009 | Ingimundarson et al. |
| 7,713,225 B2 | 5/2010 | Ingimundarson et al. |
| 7,762,973 B2 | 7/2010 | Einarsson et al. |
| 7,794,418 B2 | 9/2010 | Ingimundarson et al. |
| 7,806,842 B2 | 10/2010 | Stevenson et al. |
| 7,874,996 B2 | 1/2011 | Weinstein et al. |
| 7,905,851 B1 | 3/2011 | Bledsoe |
| 7,937,973 B2 | 5/2011 | Sorensen et al. |
| 8,016,781 B2 | 9/2011 | Ingimundarson et al. |
| 8,216,170 B2 | 7/2012 | Ingimundarson et al. |
| 8,241,234 B2 | 8/2012 | Ingimundarson et al. |
| 8,257,293 B2 | 9/2012 | Ingimundarson et al. |
| 8,267,879 B2 | 9/2012 | Ingimundarson et al. |
| 8,328,746 B2 | 12/2012 | Ingimundarson et al. |
| 8,328,747 B2 | 12/2012 | Matsunaga |
| 8,425,441 B2 | 4/2013 | Ingimundarson |
| 8,585,623 B2 | 11/2013 | Ingimundarson |
| 8,864,692 B2 | 10/2014 | Ingimundarson et al. |
| 9,220,622 B2 | 12/2015 | Ingimundarson et al. |
| 9,265,645 B2 | 2/2016 | Ingimundarson et al. |
| 9,358,146 B2 | 6/2016 | Thorsteinsdottir et al. |
| 9,364,365 B2 | 6/2016 | Omarsson et al. |
| 9,375,341 B2 | 6/2016 | Ingimundarson et al. |
| 9,474,334 B2 | 10/2016 | Jonsson et al. |
| 9,498,025 B2 | 11/2016 | Omarsson et al. |
| 9,814,615 B2 | 11/2017 | Ingimundarson |
| 2001/0020143 A1 | 9/2001 | Stark et al. |
| 2001/0056251 A1 | 12/2001 | Peters |
| 2002/0032397 A1 | 3/2002 | Coligado |
| 2002/0077574 A1 | 6/2002 | Gildersleeve et al. |
| 2002/0082542 A1 | 6/2002 | Hall |
| 2002/0095750 A1 | 7/2002 | Hammerslag |
| 2002/0132086 A1 | 9/2002 | Su-Tuan |
| 2003/0032907 A1 | 2/2003 | Prahl |
| 2003/0069531 A1 | 4/2003 | Hall |
| 2003/0204156 A1 | 10/2003 | Nelson et al. |
| 2004/0002674 A1 | 1/2004 | Sterling |
| 2004/0054311 A1 | 2/2004 | Sterling |
| 2004/0058102 A1 | 3/2004 | Baychar |
| 2004/0137178 A1 | 7/2004 | Janusson et al. |
| 2004/0137192 A1 | 7/2004 | McVicker |
| 2004/0153016 A1 | 8/2004 | Salmon et al. |
| 2004/0176715 A1 | 9/2004 | Nelson |
| 2004/0199095 A1 | 10/2004 | Frangi |
| 2004/0225245 A1 | 11/2004 | Nelson |
| 2004/0267179 A1 | 12/2004 | Lerman |
| 2005/0020951 A1 | 1/2005 | Gaylord et al. |
| 2005/0038367 A1 | 2/2005 | McCormick et al. |
| 2005/0081339 A1 | 4/2005 | Sakabayashi |
| 2005/0159691 A1 | 7/2005 | Turrini et al. |
| 2005/0160627 A1 | 7/2005 | Dalgaard et al. |
| 2005/0273025 A1 | 12/2005 | Houser |
| 2006/0015980 A1 | 1/2006 | Nordt, III et al. |
| 2006/0020237 A1 | 1/2006 | Nordt, III et al. |
| 2006/0026732 A1 | 2/2006 | Nordt, III et al. |
| 2006/0026733 A1 | 2/2006 | Nordt, III et al. |
| 2006/0026736 A1 | 2/2006 | Nordt, III et al. |
| 2006/0030802 A1 | 2/2006 | Nordt, III et al. |
| 2006/0030803 A1 | 2/2006 | Nordt, III et al. |
| 2006/0030804 A1 | 2/2006 | Nordt, III et al. |
| 2006/0030805 A1 | 2/2006 | Nordt, III et al. |
| 2006/0030806 A1 | 2/2006 | Nordt, III et al. |
| 2006/0070164 A1 | 4/2006 | Nordt, III et al. |
| 2006/0070165 A1 | 4/2006 | Nordt, III et al. |
| 2006/0084899 A1 | 4/2006 | Verkade et al. |
| 2006/0090806 A1 | 5/2006 | Friedline et al. |
| 2006/0094999 A1* | 5/2006 | Cropper ............... A61F 5/0109 602/60 |
| 2006/0116619 A1 | 6/2006 | Weinstein et al. |
| 2006/0135902 A1 | 6/2006 | Ingimundarson et al. |
| 2006/0135903 A1 | 6/2006 | Ingimundarson et al. |
| 2006/0155229 A1 | 7/2006 | Ceriani et al. |
| 2006/0156517 A1 | 7/2006 | Hammerslag et al. |
| 2006/0191110 A1 | 8/2006 | Howell et al. |
| 2007/0083136 A1 | 4/2007 | Einarsson |
| 2007/0106191 A1* | 5/2007 | Mueller ............... A61F 5/0106 602/26 |
| 2007/0130665 A1 | 6/2007 | Wang |
| 2007/0167892 A1 | 7/2007 | Gramza et al. |
| 2007/0167895 A1 | 7/2007 | Gramza et al. |
| 2007/0185425 A1 | 8/2007 | Einarsson et al. |
| 2007/0225824 A1 | 9/2007 | Einarsson |
| 2008/0034459 A1 | 2/2008 | Nordt, III et al. |
| 2008/0066272 A1 | 3/2008 | Hammerslag et al. |
| 2008/0229556 A1 | 9/2008 | Hammer |
| 2008/0294079 A1 | 11/2008 | Sterling et al. |
| 2009/0099562 A1 | 4/2009 | Ingimundarson et al. |
| 2009/0126413 A1 | 5/2009 | Sorensen et al. |
| 2010/0068464 A1 | 3/2010 | Meyer |
| 2010/0125231 A1 | 5/2010 | Knecht |

(56) References Cited

U.S. PATENT DOCUMENTS

| | | | |
|---|---|---|---|
| 2011/0057466 A1 | 3/2011 | Sachee et al. | |
| 2011/0275970 A1 | 11/2011 | Paulos et al. | |
| 2012/0010547 A1 | 1/2012 | Hinds | |
| 2012/0046585 A1 | 2/2012 | Lee et al. | |
| 2012/0090624 A1 | 4/2012 | Chang | |
| 2012/0109031 A1 | 5/2012 | Vollbrecht et al. | |
| 2012/0220910 A1 | 8/2012 | Gaylord et al. | |
| 2013/0245523 A1* | 9/2013 | Romo | A61F 5/0125 602/16 |
| 2014/0121579 A1 | 5/2014 | Hinds | |
| 2014/0194801 A1 | 7/2014 | Thorsteinsdottir et al. | |
| 2014/0214016 A1 | 7/2014 | Ingimundarson et al. | |
| 2014/0257158 A1 | 9/2014 | Lee et al. | |
| 2015/0032041 A1 | 1/2015 | Ingimundarson et al. | |
| 2015/0290014 A1* | 10/2015 | Anglada | A61F 5/0109 602/26 |
| 2016/0242945 A1 | 8/2016 | Thorsteinsdottir et al. | |
| 2016/0278959 A1 | 9/2016 | Omarsson et al. | |
| 2016/0296360 A1 | 10/2016 | Ingimundarson et al. | |
| 2017/0065037 A1 | 3/2017 | Omarsson et al. | |
| 2017/0348130 A1 | 12/2017 | Petursson | |
| 2017/0348131 A1 | 12/2017 | Petursson | |

FOREIGN PATENT DOCUMENTS

| | | |
|---|---|---|
| DE | 100 04 561 A1 | 8/2001 |
| DE | 20 2004 012 892 UI | 10/2004 |
| EP | 0 050 769 A1 | 5/1985 |
| EP | 0 196 204 A2 | 10/1986 |
| EP | 0 611 069 A | 8/1994 |
| EP | 1016351 A1 | 7/2000 |
| EP | 2612626 A2 | 7/2013 |
| FR | 2 399 811 A1 | 3/1979 |
| FR | 2 553 996 A1 | 5/1985 |
| FR | 2 766 359 A1 | 1/1999 |
| GB | 1209413 A | 10/1970 |
| GB | 2 136 294 A | 9/1984 |
| GB | 2 455 972 A | 7/2009 |
| WO | 88/01855 A1 | 3/1988 |
| WO | 94/00082 A1 | 1/1994 |
| WO | 00/49982 A1 | 8/2000 |
| WO | 00/70984 A1 | 11/2000 |
| WO | 2006/015599 A1 | 2/2006 |
| WO | 2006/069221 A2 | 6/2006 |
| WO | 2006/069222 A2 | 6/2006 |
| WO | 2008/115376 A1 | 9/2008 |
| WO | 2009052031 A1 | 4/2009 |
| WO | 2010/117749 A2 | 10/2010 |
| WO | 2011/073803 A2 | 6/2011 |

OTHER PUBLICATIONS

Advertising Brochure: "NUKO Camp", 6 pages, Camp International, Inc. Jackson, MI (1984).
Advertising Brochure: "Lerman Multi-Ligaments Knee Control Orthosis", 2 pages, Zinco Industries, Inc. of Montrose, CA (1985).
"Information on Flexible Polyurethane Foam", IN TOUCH, vol. 4, No. 3, Jul. 1994, 5 pages.
Advertisement: "Custom Engineered Fabrics and Products for Advanced High Performance", 1 page, Gehring Textiles (visited Dec. 15, 2005), http://www.gehringtextiles.com/d3.html.
Article: "Osteoarthritis of the Knee: An Information Booklet", Arthritis Research Campaign (visited Dec. 14, 2004) http://www.arc.org.uk/about_arth/booklets/6027/6027.htm.
Advertising Brochure: "Freedom to Perform-Fusion", 5 pages, (2005).
Advertising Brochure: "Fusion", 6 pages, Breg, Inc. of Vista, CA (2005).
Advertising Brochure: "Fusion XT", 2 pages, Breg, Inc. of Vista, CA (2005).
Advertising Brochure: "Anderson Knee Stabler", 4 pages, Omni Scientific, Inc. of Lafayette, CA. Feb. 7, 2013.
Advertising Brochure: "OTI Brace", 4 pages, Orthopedic Technology, Inc. of San Leandro, CA. Feb. 7, 2013.
Advertising Brochure: "The Four Axioms of Functional Bracing", 2 pages, Bledsoe by Medical Technology, Inc. (2005).
Advertising Brochure: "The Leader in Knee Motion Management," 8 pages. Donjoy, Carsbad, CA. Feb. 7, 2013.
Advertising Brochure: "The Lenox Hill Lightweight", 1page, Lenox Hill Brace, Inc., New York, NY. Feb. 7, 2013.
Advertising Brochure: "XCL System", 2 pages, Innovation Sports of Foothill Ranch, CA. Feb. 7, 2013.
Advertising Brochure: "The 9 Innovations of the Axiom Custom Brace", 1 page, Bledsoe, Medical Technology, Inc.(2005).
Technical Manual: Bellacure: Restore Your Lifestyle, 10 pages, Bellacure, Inc. (2005).
Technical Manual: "Boa Technology", 3 pages, Boa Technology, Inc. of Steamboat Springs, CO, Feb. 7, 2013.
Advertising Brochure: "GII Unloader Select", 2 pagse, Ossur HF of Reykjavik, Iceland (visited Mar. 8, 2005), http://www.ossur.com/pring.asp?pageID=1729.
Advertisement: "McDavid Knee Guard and 155 Ligament Augmentation System", 3 pages, Advanced Brace of Irving TX (visited Mar. 8, 2005), http://www.supports4u.com/mcdavid/kneeguard.htm.
Advertisement: "Triax", 1 page, Lanxess AG (visited Mar. 8, 2005), http://www.techcenter.lanxess.com/sty/emea/en/products/description/57/index/jsp?print=true&pid=57.
Reference: "Anatomical Planes", 1 page, (visited Mar. 26, 2005), http://www.spineuniverse.com/displayarticle.phpo/article1023.html.
Advertisement: "M2 Inc. Parts Catalog", 3 pages, M2 Inc. of Winooski, VT (visited Mar. 29, 2005), http://www.m2intl.com/medical.MedClsr.htm.
Advertisement: "Axiom", 3 pages, Bledsoe by Medical Technology, Inc. (visited Jun. 15, 2005), http://www.bledsoebrace.com/custom/axiom.asp.
Advertisement: "Bellacure: The Treatment Device", 6 pages, Bellacure, Inc. (visited Jan. 5, 2006), http://www.bellacure.com/products/index/html.
Advertisement: "Lerman 3-Point Knee Orthosis", 2 pages, Becker Orthopedic of Troy, MI (visited Feb. 26, 2006), http://www.beckerortho.com/knee/3-point/htm.
International Search Report and Written Opinion from International Application No. PCT/US08103237, dated Jul. 14, 2008, 10 pages.
Article: "Thermoplastic Elastomers TPE, TPR, TPV", 6 pages (visited Mar. 14, 2007), http://www.bpf.co.uk.bpfindustry/plastics_thermplasrubber_TBR.cfm.
European Search Report Issued in EP 10 17 2396, dated Oct. 25, 2010, 5 pages.
European Search Report Issued in EP 08 74 2047, dated Aug. 1, 2013, 6 pages.
International Search Report and Written Opinion from International Application No. PCT/IB2010/003540, dated Oct. 13, 2011, 6 pages.
International Search Report and Written Opinion International Application No. PCT/US2014/010410, dated May 2, 2014.
International Search Report and Written Opinion of the International Searching Authority from International Application No. PCT/US2014/014192, dated May 20, 2014.
International Search Report and Written Opinion from International Application No. PCT/US2013/069558, dated Jul. 3, 2014.
International Search Report and Written Opinion from International Application No. PCT/US2014/010407, dated Jul. 10, 2014.
International Search Report and Written Opinion from International Application No. PCT/US2014/033266, dated Jul. 23, 2014.
"VELSTICK semi-rigid FASTENER Furnished in Separate, Mating Components", VELCRO Fasteners, Spaenaur, Sep. 2, 2009, 1 Page.
International Preliminary Report on Patentability From PCT Application No. PCT/US2016/012346, dated Jul. 11, 2017.
International Search Report from PCT Application No. PCT/US2016/012346, dated May 6, 2016.
International Search Report from PCT Application No. PCT/US2017/036073, dated Nov. 22, 2017.

\* cited by examiner

ORTHOPEDIC DEVICE FOR TREATING OSTEOARTHRITIS OF THE KNEE

FIELD OF THE DISCLOSURE

The disclosure relates to orthopedic devices, and more particularly to a knee brace or wrap arranged for unloading a knee for treatment of osteoarthritis.

BACKGROUND

Known orthopedic devices are used for providing stability, protection, support, rehabilitation and/or unloading a portion of the human anatomy. These devices, however, are often considered as being physically bulky, heavy, and costly requiring numerous manufacturing processes to be produced.

An example of an orthopedic device is a knee brace. As is well understood, knee braces are widely used to treat a variety of knee infirmities. Such braces may be configured to impart forces or leverage on the limbs surrounding the knee joint to relieve compressive forces within a portion of the knee joint, or to reduce the load on that portion of the knee. If knee ligaments are weak and infirm, a knee brace may stabilize, protect, support, unload, and/or rehabilitate the knee.

The knee is acknowledged as one of the weakest joints in the body and serves as the articulating joint between the thigh and calf muscle groups. The knee is held together primarily by small but powerful ligaments. Knee instability arising out of cartilage damage, ligament strain, and other causes is relatively commonplace since the knee joint is subjected to significant loads during the course of almost any physical activity requiring legs.

A healthy knee has an even distribution of pressure in both its medial and lateral compartments. It is normal for a person with a healthy knee to place a varus moment on the knee when standing so pressure between the medial and lateral compartments is uneven but still natural.

Compartmental osteoarthritis is a problematic knee infirmity, and may arise when there is a persistent uneven distribution of pressure in one of the medial and lateral compartments of the knee. Compartmental osteoarthritis can be caused by injury, obesity, misalignment of the knee, or due to aging of the knee. A major problem resulting from osteoarthritis is that smooth cartilage lining the inside of the knee wears away. This leads to a narrowing of the joint space due to the development of cysts and erosions in the bone ends. Because of the narrowing of the joint, bone comes directly in contact with bone, and an uneven distribution of pressure develops across the knee, which may cause the formation of bone spurs around the joint. All of these changes ultimately lead to increasing pain and stiffness of the joint.

While there are no cures to osteoarthritis, there are many treatments. Individuals who have a diagnosis of isolated lateral or medial compartmental osteoarthritis of the knee are confronted with a variety of treatment options such as medications, surgery, and nonsurgical interventions. Nonsurgical interventions include using canes, lateral shoe wedges, and knee braces.

Knee bracing is useful in providing compartment pain relief by reducing the load on the compartment through applying an opposing external valgus or varus moment about the knee joint. Unloading knee braces have been shown to significantly reduce osteoarthritis knee pain while improving knee function. U.S. Pat. No. 5,277,698, granted Jan. 11, 1994, describes a brace having rigid upper and lower cuffs connected to one another by a hinge assembly, and a diagonal or helical dynamic force strap arranged to generate a three-point leverage system that unloads a compartment of the knee. Alternatively, U.S. Pat. No. 7,198,610, granted Apr. 3, 2007, describes a variation of the three-point leverage system in U.S. Pat. No. 5,277,698, including flexible uprights connected by a hinge assembly, and dual dynamic force straps used to disperse counterforces across two points of contact on a leg to unload a compartment of the knee. U.S. Pat. Nos. 5,277,698 and 7,198,610 are incorporated herein by reference in their entirety.

Individuals suffering from osteoarthritis of the knee have varying degrees of discomfort and undergo stages of worsening osteoarthritis. Many of the known unloading braces may be too aggressive, unnecessary for individuals with minor osteoarthritis, moderate or mild knee ligament instabilities, and may require cost-effective solutions. Rather than significant forces urged on the knee by a dynamic unloading strap, the individuals require a combination of support on the knee with some unloading capabilities. Such individuals may require a streamlined brace that is durable while having minimal impact on activities and clothing selections. h is yet further desirable that the knee brace has lightweight shells and the brace can be moderately adjusted for differences in patient anatomy and accommodate a wide range of varus/valgus alignments enabling on-the-fly adjustability for unloading force and compressive forces on the leg and knee.

Various soft-good or sleeve braces exist to assist persons with damaged muscle tissue, cartilage and ligaments in the knee area, but few treat osteoarthritis of the knee, particularly with a dynamic force strap. The sleeve braces often rely on elasticity of the sleeve to snugly hold the knee by enclosing the knee in either a tubular configuration or a wrap-type brace that is openable and wraps about the knee to form a tubular configuration.

An advantage of the soft braces is that the tubular configuration may apply radial compression to the knee, and straps may increase the radial compression on the knee. Disadvantages occur in that the stretchability of the soft braces may be too tight, and either is too restrictive or insufficiently restrictive to movement. Various strapping arrangements have been proposed that attempt to cure the deficiencies but many lack flexibility in strapping along various portions of the leg and insufficiently accommodate a wearer's leg anatomy.

Few knee braces have been able to harmonize effective unloading of the knee in combination with a sleeve-type brace without the necessity of a substantial frame system. In the instance of a dynamic force strap, it has been difficult to present a solution that mitigates rotation and migration of the sleeve from unloading of the knee by a dynamic force strap, while providing therapeutic compression and augmenting the dynamic force strap.

SUMMARY

It is among the objects of the orthopedic device of the disclosure to provide a knee brace of the unloading type which harmonizes the use of a dynamic force strap with a sleeve-type brace to unload a knee having osteoarthritis while resisting rotation caused by the dynamic force strap and attendant use of the knee brace, and affording sufficient compression about the leg and knee with sufficient adjustability and accommodation to various unique anatomies.

The compressive support offered by the sleeve-type brace is most effective at improving stability of the knee and is maximized in full flexion since most compression occurs in full flexion. Indeed, the compression is most effective when the force strap is least effective in full flexion, and is less effective when the force strap is most effective in full extension. By trading in effectiveness depending on extension and flexion, the sleeve-type brace and the force strap are able to improve the efficacy of unloading a knee and providing requisite support over the stages of a person's gait in a simple and low cost manner.

The orthopedic device is generally provided for low active users with mild-to-moderate symptoms of unicompartmental osteoarthritis, although it is not limited to such use. The closure system of the orthopedic device is provided to assist patients with poor hand strength or dexterity. The orthopedic device has a wrap-around design arranged for easily wrapping about a wearer's leg, and enables a simple donning procedure. Unloading of the wearer's knee by the orthopedic device is achieved by a dynamic force strap which is simple to adjust and provides gentle force applied to the knee.

In an embodiment, the orthopedic device includes a first panel defining opposed first and second sides, and a second panel having a first end secured to the first side of the first panel along a seam, and a second end securable to the second side of the first panel at a location site. A first strap has a first end secured to the first side of the first panel along the seam and overlies the second panel, and a second end securable to the second side of the first panel at the location site.

A dynamic force strap helically extends between upper and lower portions of the orthopedic device and connects to the first panel. A hinge assembly secures to the first panel and extends between upper and lower portions of the orthopedic device. The dynamic force strap has first and second ends securing to first and second frames of the hinge assembly spaced apart by first and second struts connected to one another by a hinge.

The first strap preferably extends obliquely from the seam and relative to the first panel. The seam defines a profile with at least one curved segment, and the first strap is located along the curved segment. A second strap preferably extends from a lower portion of the seam and the first strap extends from an upper portion of the seam at an oblique angle relative to the second strap. A lower edge of the first strap may extend in a substantially straight direction from the first panel and an upper edge of the first strap may extend at an oblique angle relative to the first panel. A clearance may be defined between the first and second straps, and the clearance is greatest in height at the seam and tapers in height toward second ends of the first and second straps. The first strap may have a longer length than a length of the second strap.

The second panel preferably defines at least one flap located at the second end. The at least one flap may include fastener material for engaging corresponding fastener material located at a second side of the first panel. For example, the at least one flap may comprise first and second flaps spaced apart by a gap so that a patella opening is formed in combination with the second side of the first panel. The second side of the first panel preferably defines first and second projecting portions spaced by a notch combining with the gap to form the patella opening.

According to an embodiment, in an open, flat configuration, the first flap is located at least in part above the second end of the first strap, and the second flap is located at least in part above the second end of the second strap relative to the upper corner of the seam. In a closed, wrapped configuration, the first flap is located below the second end of the first strap and borders the patella opening of the orthopedic device. Tensioning of the first and second straps is arranged independently of tensioning of the second panel via the first and second flaps. The first strap is arranged to be secured to the second side of the first panel independently from the second strap such that the first and second straps are separated by a clearance at the seam. When tensioning the first and second flaps to secure to the second side of the first panel, first and second edges of the second panel may slope downwardly and upwardly from the upper and lower corners, respectively, toward the second side of the first panel.

The straps and the flaps have various spatial relationships enabling improved tensioning of the straps and embrace over the leg and about the knee of the wearer.

A method for securing an orthopedic device to a leg and about a knee may involve using the orthopedic device by placing the orthopedic device in a flat configuration posterior of the knee and leg; locating the seam along a posterior or a second side of the knee and leg; wrapping the first panel from the seam about a first side of the leg and knee; wrapping the second panel from the seam about a second side of the leg and knee; securing a second end of the second panel to a second side of the first panel; wrapping the first strap from the seam independently from the second panel and securing a second end to the second side of the first panel and overlying at least part of the second panel.

The numerous advantages, features, and functions of embodiments of the orthopedic device will become readily apparent and better understood in view of the following description and accompanying drawings. The following description is not intended to limit the scope of the orthopedic device, but instead merely provides exemplary embodiments for ease of understanding.

The drawing figures are not necessarily drawn to scale, but instead are drawn to provide a better understanding of the components, and are not intended to be limiting in scope, but rather to provide exemplary illustrations. The figures illustrate exemplary configurations of an orthopedic device, and in no way limit the structures or configurations of an orthopedic device and components according to the present disclosure.

DETAILED DESCRIPTION OF VARIOUS EMBODIMENTS

A. Environment and Context

An embodiment of an orthopedic device in a knee brace is provided to reduce the effect of osteoarthritis in a knee joint and/or stabilize a knee joint weakened by injury or other infirmities. Although the illustrated embodiments show a hinge positioned on the medial side of the knee brace and the straps positioned on the lateral side of the knee brace, it will be understood that the knee brace may be configured to reduce or cure both medial and lateral knee joint infirmities. The hinge may be positioned on the lateral side of the knee brace and the straps may be positioned on the medial side of the knee brace.

The knee brace embodiments of the disclosure are adapted for a human knee joint, and may be dimensioned to accommodate different types, shapes, and sizes of human joints, appendages, and other anatomical portions. Embodiments may be provided to orient principal forces exerted by strap systems of the embodiments at any desirable location to treat knee infirmities.

While the disclosure is susceptible to various modifications and alternative constructions, certain illustrative embodiments are in the drawings and are described below. It should be understood, however, there is no intention to limit the disclosure to the embodiments disclosed, but on the contrary, the invention covers all modifications, alternative constructions, combinations, and equivalents falling within the spirit and scope of the disclosure. It will be understood that, unless a term is defined to possess a described meaning, there is no intent to limit the meaning of such term, either expressly or indirectly, beyond its plain or ordinary meaning B. Definitions For ease of understanding the disclosed embodiments of an orthopedic device, the anterior and posterior portions of the orthopedic device may be described independently. Anterior and posterior portions of the orthopedic device function together to support and stabilize anatomical portions of the user of the device.

For further ease of understanding the embodiments of an orthopedic device as disclosed, a description of a few terms, when used, is necessary. As used, the term "proximal" has its ordinary meaning and refers to a location next to or near the point of attachment or origin or a central point, or located toward the center of the body. Likewise, the term "distal" has its ordinary meaning and refers to a location situated away from the point of attachment or origin or a central point, or located away from the center of the body. The term "posterior" also has its ordinary meaning and refers to a location behind or to the rear of another location. Lastly, the term "anterior" has its ordinary meaning and refers to a location ahead of or to the front of another location.

The terms "rigid" and "flexible" may distinguish characteristics of portions of certain features of the orthopedic device. The term "rigid" should denote an element of the device is devoid of flexibility. Within the context of frame or support members or shells that are "rigid," it should indicate that they do not lose their overall shape when force is applied, and they may break if bent with sufficient force. The term "flexible" should denote that features are capable of repeated bending such that the features may be bent into retained shapes or the features retain no general shape, but continuously deform when force is applied.

As for the term "semi-rigid," this term is used to connote properties of support members or shells that provide support and are free-standing; however such support members or shells may have a degree of flexibility or resiliency.

Fastener material is used to denote any material or system for adjustably and removably securing two pieces together. An exemplary fastener material is hook and loop fastener material and any combination thereof.

C. Description of Orthopedic Device Embodiments

Referring to the embodiment of FIGS. 1-4, an orthopedic device 10 is in a knee brace and is both an unloading and sleeve type brace. The orthopedic device is not limited to a knee brace, but its various features may be incorporated in other types of orthopedic devices.

As illustrated, the orthopedic device 10 has a first panel 12 defining opposed first and second sides 13, 39. A second panel 14 having a first end 15 is secured to the first side 13 of the first panel 12 along a seam 48, and a second end 27 is securable to the second side 39 of the first panel 12 at a location site 56, 58, such as first and second loop parts. The location site preferably includes fastener material and is inelastic to inhibit rotational movement and stretching at the interface where the second panel and first and seconds straps secure to the first panel. A first strap 20 has a first end 21 secured to the first side 13 of the first panel 12 along the seam 48 and overlies the second panel 14, and a second end 31 is securable to the second side 39 of the first panel 12 at the location site 56, 58. A second strap 22 has a first end 23 secured to the first side 13 of the first panel 12 and extends from a lower portion of the seam 48. The first strap 20 extends from an upper portion of the seam 48 at an oblique angle 72 relative to an angle 74 of the second strap 22. The oblique angle 72 is also relative to the angle 70 of the edge 60 of the first panel 12 as the first strap 20 extends downwardly from the seam 48 and departs from the profile of the first panel.

Figure 3:
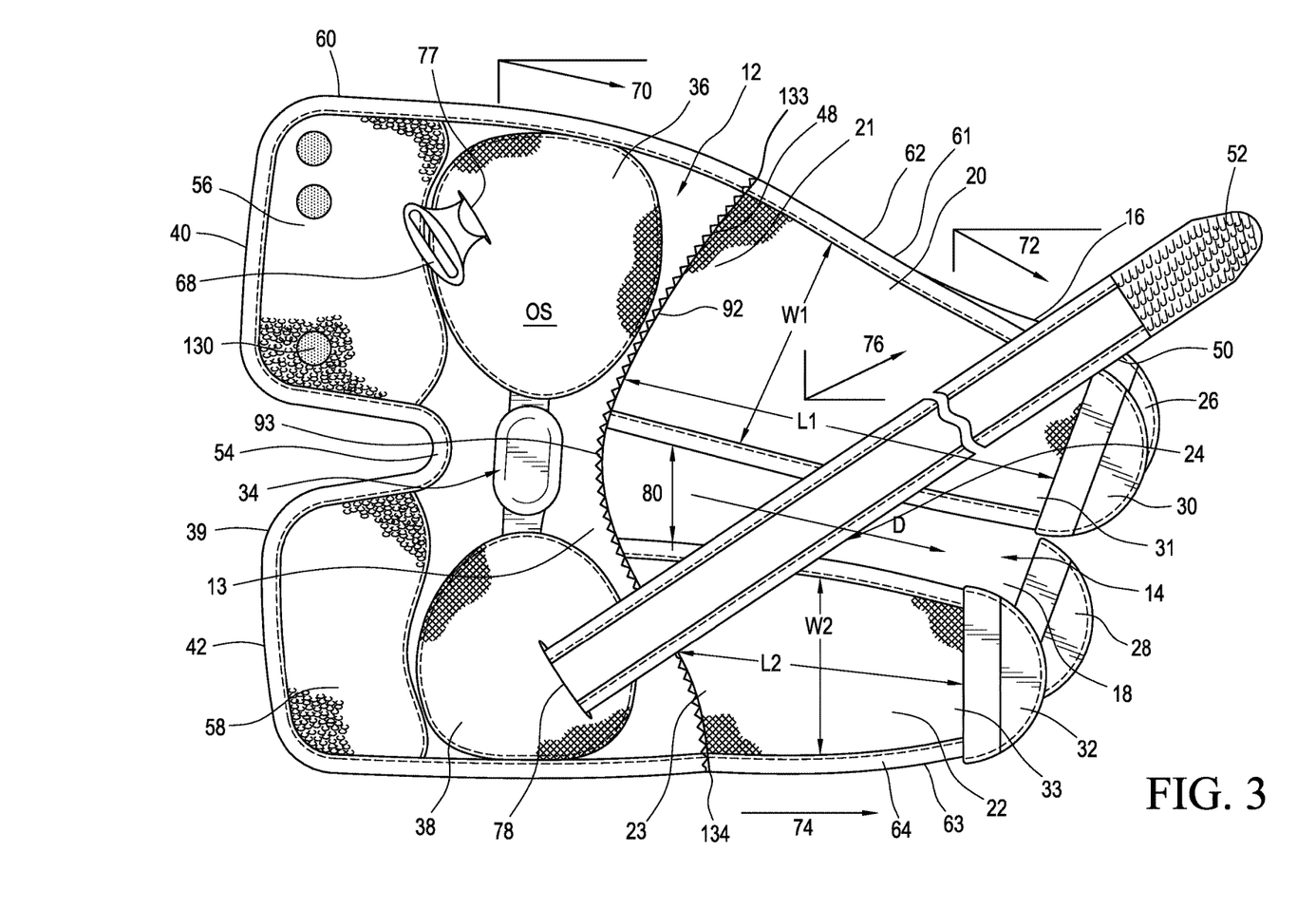
FIG. 3 is a plan view of the outer side of the orthopedic device of FIG. 1 in an open configuration.

As shown in FIG. 3, in an open, flat configuration, the first flap 16 is at least in part above the second end 31 of the first strap 20, and the second flap 18 is at least in part above the second end 33 of the second strap 22 relative to the upper corner 133 of the seam 48. In a closed, wrapped configuration depicted in FIG. 1, the first flap 26 is below the second end 31 of the first strap 20 and borders a patella opening 44 of the orthopedic device 10.

Figure 1:
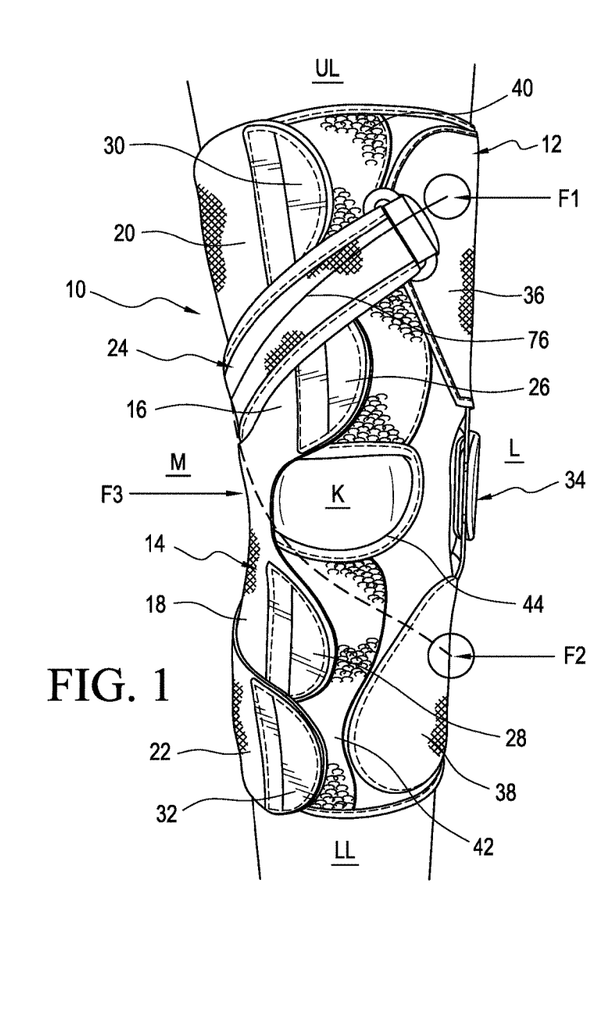
FIG. 1 is a front elevational view of an embodiment of the orthopedic device in a closed configuration.

Tensioning of the first and second straps 20, 22 is preferably arranged independently of tensioning of the second panel 14 via the first and second flaps 16, 18. The first strap 20 is arranged to be secured to the second side 39 of the first panel 12 independently from the second strap 22 such that the first and second straps 20, 22 are separated by a clearance 80 at the seam 48.

The independent tensioning of the first and second straps 20, 22 connotes that the wrapping and tensioning of one of the straps does not impact the other strap. This has the advantage of enabling more adjustment possibilities above and below the knee, and reduces migration and rotation of the brace since one can tailor the tensioning of each strap irrespective of the other.

The first and second flaps 26, 28 are tensioned on the leg by securing to the second side 39 of the first panel 12. The first and second edges 98, 102 of the second panel 14 slope downwardly and upwardly from the upper and lower corners 133, 134, respectively, toward the second side of the first panel 12.

The second panel 14 is independent from the first and second straps, as it secures and extends from the seam 48 freely without influence of the first and seconds straps. The second panel is not secured to either of the first and second straps, and the first and second straps only overlie the second panel when secured to the second side of the first panel. The orientation of the second panel relative to the knee permits dynamic support to the knee through compression, and the first and second edges 98, 102 are asymmetric to better conform to the leg anatomy rather than a uniformly shaped panel.

The combination of the first and second panels and first and second straps enables a versatile knee brace without the necessity of additional straps that snugly and compressively embrace the leg and knee of a wearer. The arrangement of the first and second panel and the first and second straps enable wrapping about the leg and knee without structural components and not restricting knee movement. Adjustment of the straps enables initial easy and instantaneous application of the knee brace in the right location and disposition, and further on the fly adjustment by the wearer.

Figure 2:
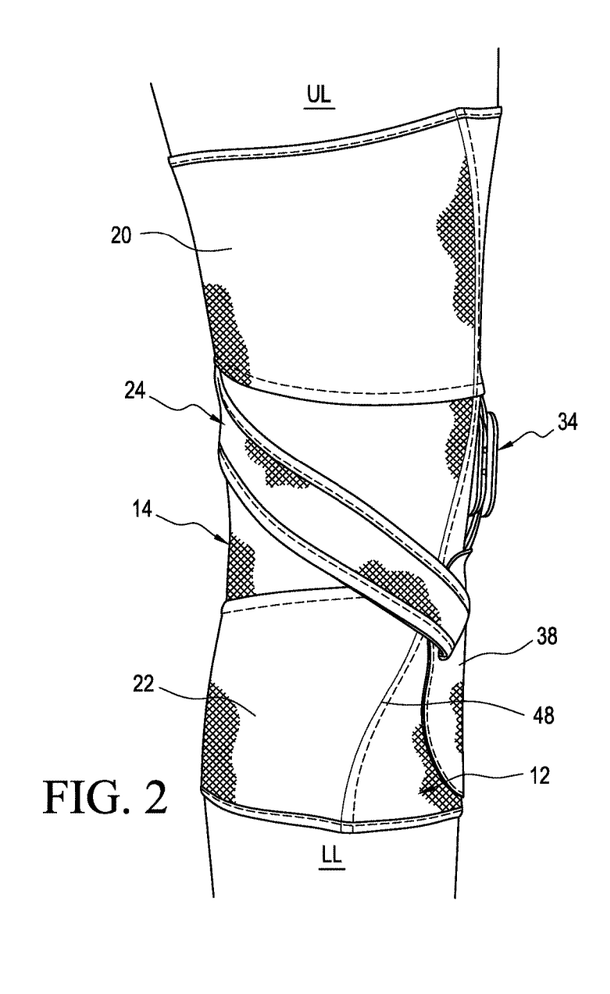
FIG. 2 is a rear elevational view of the orthopedic device of FIG. 2.

A dynamic force strap 24 helically extends between upper and lower portions of the orthopedic device 10 and a hinge assembly 34 secured to the first panel 12 and extending between upper and lower portions of the orthopedic device 10. The dynamic force strap 24 has first and second ends securing to first and second frames 112, 114 of the hinge assembly 34 spaced apart by first and second struts 108, 110 connected to one another by a hinge 106. The first and second struts 108, 110 are preferably malleable to allow a clinician to modify the orthopedic device according to specific anatomy of a wearer.

The dynamic force strap 24 extends obliquely or helically about the first panel 12, second panel 14 and the first and second straps 20, 22 at a generic angle or orientation 76, but it is understood the angle may be adjusted according to the anatomy of a wearer of the knee brace. The dynamic force strap is preferably inelastic.

Figure 4:
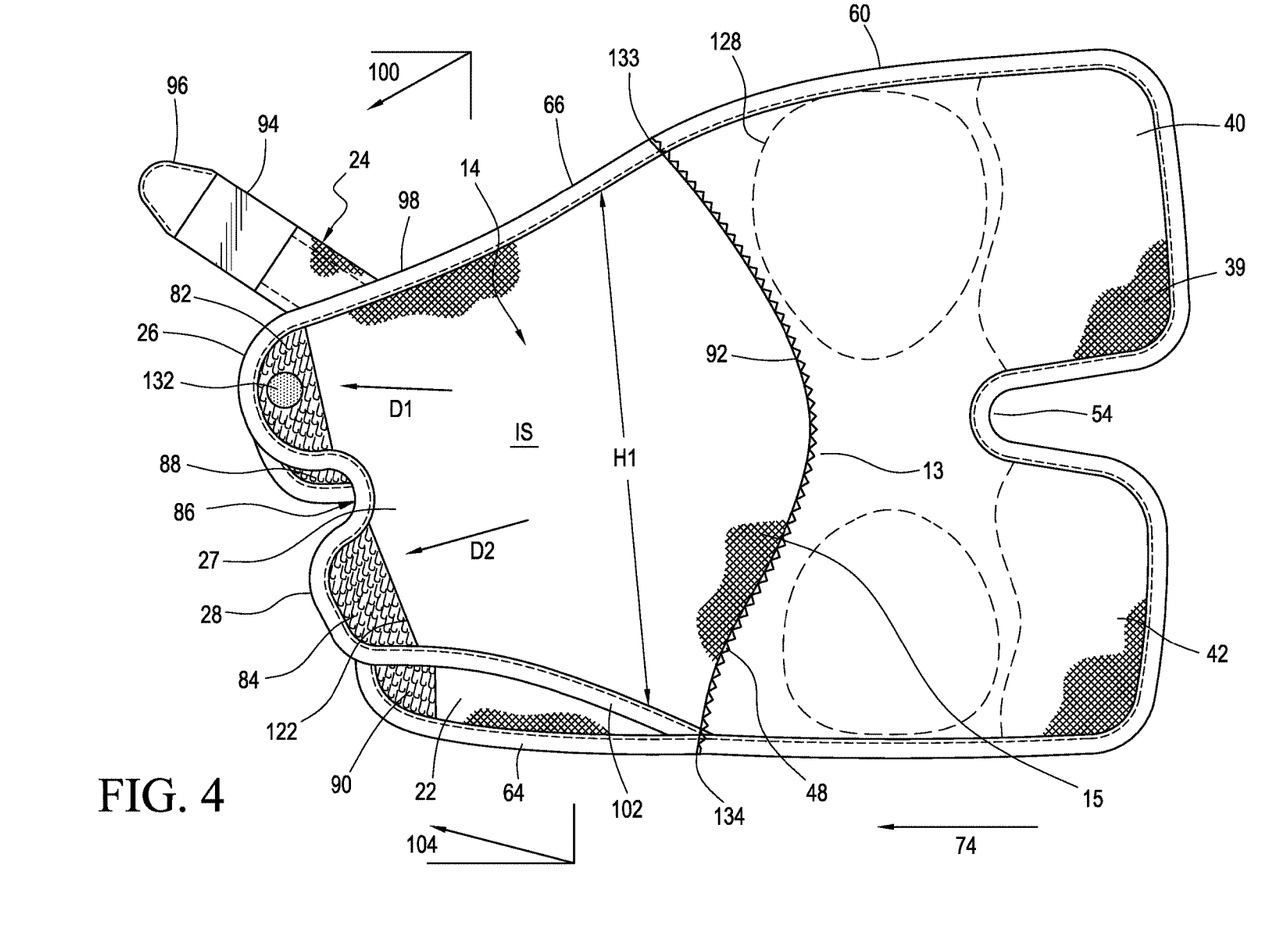
FIG. 4 is a plan view of the inner side of the orthopedic device of FIG. 1 in an open configuration.

The first panel 12 defines first and second pockets 36, 38 for removably receiving the first and second frames 112, 114. Access to the pockets 36, 38 is preferably available from the outer side OS of the orthopedic device, but may be configured for access from the inside side IS. The pockets 36, 38 are preferably formed from inelastic material secured to the first panel 12 preferably elastic and stretchable. The inelastic material of the pockets 36, 38 minimizes movement of the first and second frame 112, 114, particularly when the dynamic force strap 24 is tensioned. The outer surface of the pockets 36, 38 may include slits 77, 78 for accommodating extension of the dynamic force strap.

The inner side of the panel may include a frictional feature 128, such as silicone, arranged in combination with the first and second frames 112, 114 to mitigate rotation of the brace on the leg of a wearer. The frictional feature 128 may take a variety of shapes and patterns. For example, FIG. 4 shows how the frictional feature 128 generally corresponds to the profile of the first and second frames, and the base of projecting portions 40, 42 of the first panel 12.

Figure 5:
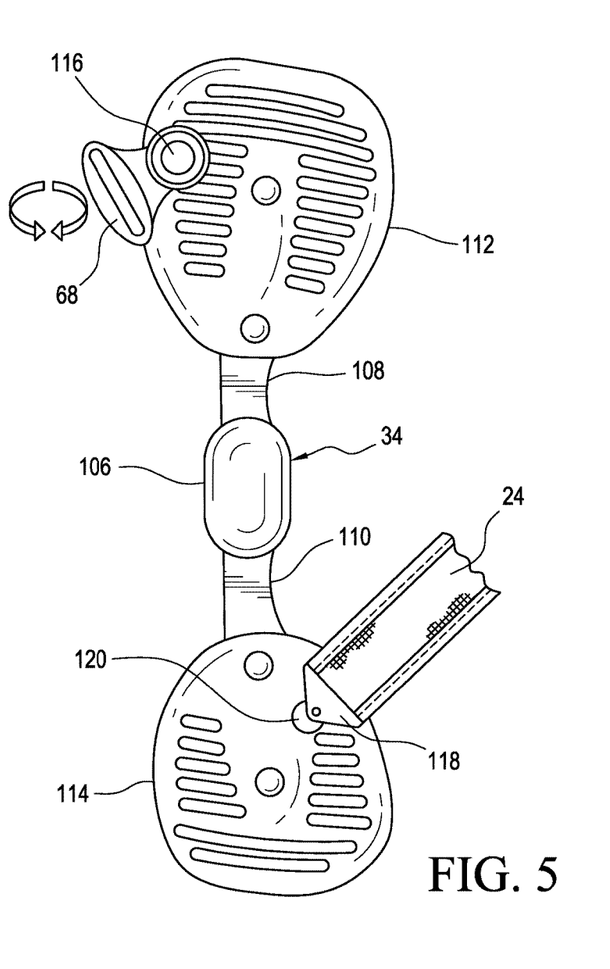
FIG. 5 is an elevational view of a hinge assembly in the orthopedic device of FIG. 1.

FIG. 5 illustrates a first bracket 68 is rotatably secured to the first frame 112 by a swivel 116, and a second bracket 118 is releasably and rotatably secured to the second frame 114 by an opening 120. The first and second ends of the dynamic force strap 24 secure to the first and second brackets 68, 118, respectively, such that the first end 52 loops around the first bracket 68 and secures to the length 50 of the dynamic force strap 24 including fastener material. The first end 52 may include a tip 96 and a main segment 94 on an outer side of the strap 24, and fastener material on the inner side for securing to the length 50 of the strap 24.

The hinge assembly and the dynamic force strap may be arranged under U.S. patent application publication 2014/0214016, published Jul. 31, 2014, and U.S. patent application publication 2014/0194801, published Jul. 10, 2014, each of which is incorporated by reference in its entirety.

As shown in FIG. 2, the hinge assembly 34 is on the lateral side L of the leg, and the dynamic force strap 24 preferably extends from the lateral side L of the brace at the lower leg LL, posterior of the knee K to the medial side M, and reaching across the upper leg UL to secure to the lateral side L of the hinge assembly. In this arrangement, the dynamic force strap is adapted to unload the lateral compartment of the knee. The knee brace may be modified by reversal of the dynamic force strap to treat medial compartmental osteoarthritis of the knee. For example, the hinge is place medially for medial compartment osteoarthritis and laterally for lateral compartment osteoarthritis, with the hinge preferably being placed slightly above the mid-point of the patella. While only one dynamic force strap is shown, the knee brace may be modified to accommodate two dynamic force straps, as taught in U.S. Pat. No. 7,198,610.

Reverting to the open configuration in FIGS. 3 and 4, the seam 48 defines a profile 92 with at least one curved segment and the first strap 20 along the curved segment. FIG. 2 exemplifies how the seam 48 preferably extends on the lateral side of the medial-lateral plane on the posterior of the knee brace to enable longer first and second straps and the second panel for providing enhanced compression. The seam 48 preferably is located just past the pockets 36, 38 so the first and second frames 112, 114 may serve as an anchor to the first panel and improves tensioning of the first and second straps and the second panel.

A lower edge of the first strap 20 extends in a substantially straight direction from the first panel 12 and an upper edge of the first strap 20 preferably extends at an oblique angle relative to the first panel 12. The clearance 80 is defined between the first and second straps 20, 22 such that the clearance 80 is preferably greatest in height at the seam and tapers in height toward second ends 31, 33 of the first and second straps 20, 22.

The geometry of the first and second straps 20, 22 advantageously improve securing the knee brace on the wearer by including geometries that accommodate the anatomy of the wearer and enable dynamic support of the knee through compression and between flexion and extension. The first strap 20 has a longer length L1 than a length L2 of the second strap 22 and the first strap 20 has an asymmetric width W1 decreasing from the seam 48 to the second end 31. The second strap 22 may have a symmetric or an asymmetric width W2 decreasing from the seam 48 to the second end 33. The seam 48 may have a curved profile 92, and an inflection point 93 of the curved profile 92 is located cross the clearance 80 at the seam 48.

A first strap tab 30 depends from the second edge 31 of the first strap 20, and the first strap tab 30 defines a handle 121 on a first side and a fastener material on a second side for securing to the location site 56, 58 on the first panel 12. The handle 121 may comprise a plastic, rubber or other suitable material for gripping and grasping. The second strap tab 32 of the second strap 22, and the tabs 26, 28 of the first and second flaps 16, 18 may be similarly formed and sized the same, and include fastener material 88, 90. The handle 121 may be secured to one of the first and second straps and first and second tabs by an edgebind or stitching 122 that is elastic or inelastic.

Figure 6:
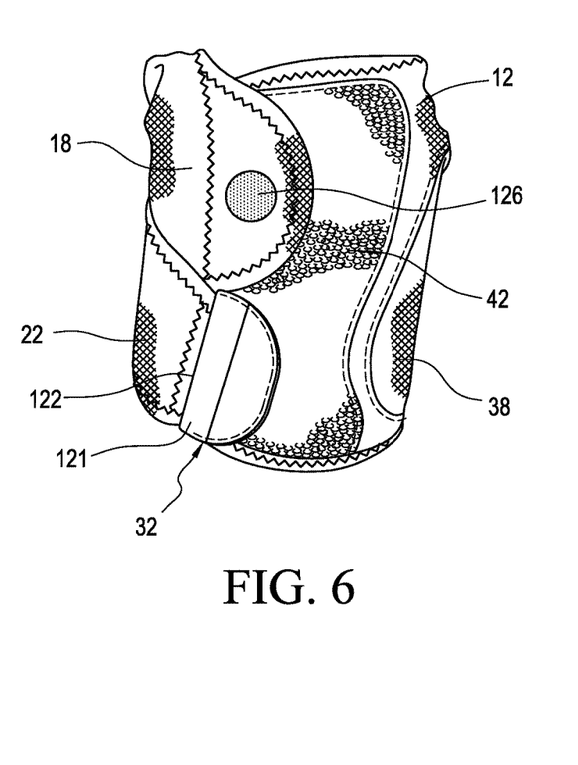
FIG. 6 is a schematic view of a variation of a tab in the orthopedic device of FIG. 1.

Referring to FIG. 6, a variation of the handle includes an opening 126 at the tabs, either reinforced with a handle or cut into the material forming the straps and flaps.

The second panel 14 is geometrically arranged to improve accommodation to the anatomy of wearer, provide effective compression of the knee dynamically between flexion and extension, and reduce migration and rotation of the brace. The second panel 14 is preferably secured to the entire seam 48 and an edge of the first side 13 of the first panel 12. The second panel 14 may taper in height H1 from upper and lower corners 133, 134 of the seam 48. The second panel 14 has a maximum height between upper and lower corners 133, 134 of the seam 48, the seam 48 having a profile 92 with a curved segment convex at the first end 15 of the second panel 14.

The first and second flaps 26, 28 are below and above upper and lower corners 133, 134, respectively, of the seam 48. The first and second flaps 26, 28 are preferably spaced apart by gap 86 so the patella opening 44 is formed in combination with the projecting portions 40, 42 spaced by a notch 54 of the first panel 12. The arrangement of the first and second flaps 26, 28 improves patella stability particularly since each of the first and second flaps 26, 28 can be individually tightened above and below the patella of the knee K. The first and second flaps 26, 28 may extend in first and second directions D1, D2 different from one another.

The first and second edges 98, 102 of the second panel 14 may extend from the seam 48 arranged at first and second angles 100, 104 oriented differently from one another. The first and second edges 98, 102 may define a curvature extending to one of first and second flaps 26, 28 at the second end 27 of the second panel 14. Each of the first and second flaps 26, 28 includes fastener material 82, 84 for engaging corresponding fastener material at the location sites 56, 58 of the first panel 12.

At least one of the first and second flaps 26, 28 includes indicia 132 corresponding to indicia 130 on the second side 39 of the first panel 12. The indicia are depicted with geometrical patterns and may be appropriately colored according to the respective location sites and tabs of the second panel and first and second straps. Other suitable indicia may identify the preferable locations for securing the tabs.

The first and second panels and the first and second straps are preferably formed from an elastic material. The elasticity of the material forming the panels and straps improve the radial compression on the leg and enable dynamic support to the knee when the compression peaks in full flexion of the knee. The edge binding 60 of the first panel edge 61, the edge binding 62 of the first strap edge 61, the edge binding 64 of the second strap edge 63, and the second panel edge binding 66 may likewise be elastic as with the other components.

The material used for first and second panels, straps is preferably a laminated Lycra-type material, laminated with net glue for optimized breathability. Material for pockets is laminated textured Lycra(outside) and loop material(inside). The textured Lycra is preferably chosen for look and the loop material on the inside is arranged to close the pockets.

Figure 7:
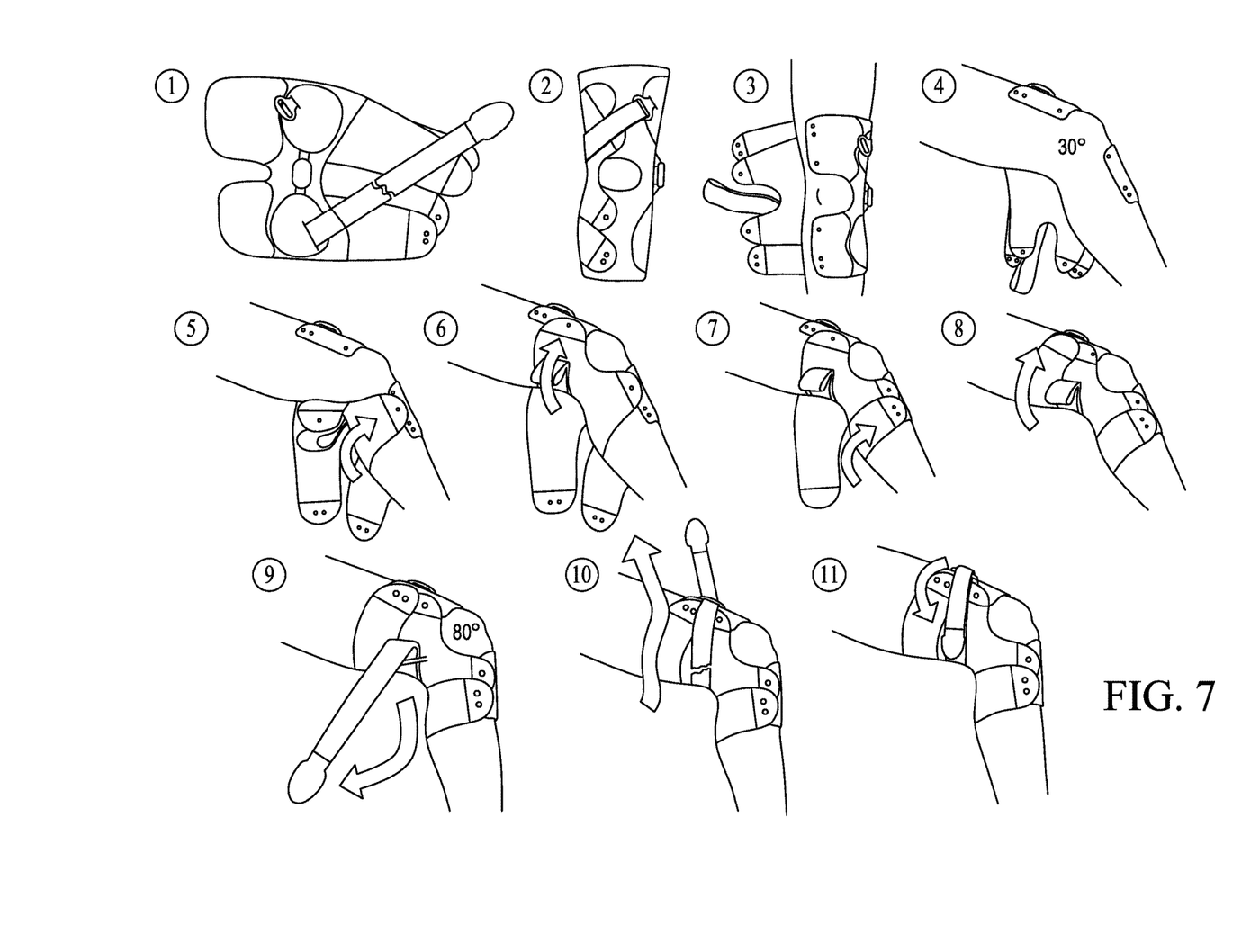
FIG. 7 is a set of schematic views showing the method for donning the orthopedic device of FIG. 1.

Referring to FIG. 7, a method is shown for securing the orthopedic device to a leg and about a knee. The method includes placing the orthopedic device 10 in a flat configuration posterior of the knee and leg. The seam 48 is positioned along posterior and lateral sides of the knee and leg, and the hinge assembly 34 is on the medial side of the knee. The first panel 12 is wrapped from the seam 48 about the lateral side of the leg and knee. The second panel 14 is wrapped from the seam 48 about the lateral side of the leg and knee, and the second end 27 of the second panel 14 is secured to a second side 39 of the first panel 12. The second flap 18 is preferably below the knee and secured to the first panel before the first flap. The first flap 26 is then secured to the second side of the first panel 12 by angling the first flap at an oblique angle toward the second side of the first panel 12 from an upper corner 133 of the seam 48.

The second strap 22 is wrapped about the leg and secured to the second side of the first panel 12 independently from the first strap 20 preferably before securing the first strap 20. The first strap 20 is then wrapped from the seam 48 independently from the second panel 14 and secured on a second end 31 to the second side 39 of the first panel 12 while overlying at least part of the second panel 14.

The dynamic force strap 24 is secured to one of upper and lower portions of the orthopedic device 10, and helically between the upper and lower portions of the orthopedic device over at least the posterior side of the knee, while securing to the hinge assembly 34 above and below the knee K, preferably at the first and second frame 112, 114. The dynamic force strap 24 is preferably looped about a first bracket 68 and rotatably secured to the first frame member 112 after the first strap 20 and the second panel 14 are secured to the second side of the first panel 12.

It is to be understood that not necessarily all objects or advantages may be achieved under any embodiment of the disclosure. For example, those skilled in the art will recognize that the orthopedic device may be embodied or carried out in a manner that achieves or optimizes one advantage or group of advantages as taught without achieving other objects or advantages as taught or suggested.

The skilled artisan will recognize the interchangeability of various disclosed features. Besides the variations described, other known equivalents for each feature can be mixed and matched by one of ordinary skill in this art to construct an orthopedic device under principles of the present disclosure. It will be understood by the skilled artisan that the features described may be adapted to other types of orthopedic devices. Hence this disclosure and the embodiments and variations thereof are not limited to knee braces, but can be utilized in any orthopedic devices.

Although this disclosure describes certain exemplary embodiments and examples of an orthopedic device, it therefore will be understood by those skilled in the art that the present disclosure extends beyond the specifically disclosed knee brace embodiments to other alternative embodiments and/or uses of the disclosure and obvious modifications and equivalents thereof. It is intended that the present disclosure should not be limited by the particular disclosed embodiments described above, and may be extended to orthopedic devices and supports, and other applications that may employ the features described.

The invention claimed is:
1. An orthopedic device, comprising:
a first panel defining opposed first and second sides;
a second panel having a first end secured to the first side of the first panel along a seam, and a second end securable to the second side of the first panel at a location site;
a first strap having a first end secured to the first side of the first panel along the seam and overlying the second panel, and a second end securable to the second side of the first panel at the location site a hinge assembly secured to the first panel and extending between upper and lower portions of the orthopedic device, wherein the first strap extends obliquely from the seam and relative to the first panel and a second strap extending from a lower portion of the seam and the first strap extending from an upper portion of the seam at an oblique angle relative to the second strap.
2. The orthopedic device of claim 1, further comprising a dynamic force strap helically extending between upper and lower portions of the orthopedic device and connecting to the first panel.
3. The orthopedic device of claim 1, wherein the seam defines a profile with at least one curved segment, the first strap located along the curved segment.

4. The orthopedic device of claim 1, wherein a lower edge of the first strap extends in a substantially straight direction from the first panel and an upper edge of the first strap extends at an oblique angle relative to the first panel.

5. The orthopedic device of claim 1, wherein a clearance is defined between the first and second straps, the clearance is greatest in height at the seam and tapers in height toward second ends of the first and second straps.

6. The orthopedic device of claim 1, wherein the first strap has a longer length than a length of the second strap.

7. The orthopedic device of claim 1, wherein the second panel defines at least one flap located at the second end, the at least one flap including fastener material for engaging corresponding fastener material located at a second side of the first panel.

8. The orthopedic device of claim 7, wherein the at least one flap includes first and second flaps spaced apart by a gap so that a patella opening is formed in combination with the second side of the first panel.

9. The orthopedic device of claim 8, wherein the second side of the first panel defines first and second projecting portions spaced by a notch combining with the gap to form the patella opening.

10. An orthopedic device, comprising:
a first panel defining opposed first and second sides;
a second panel having a first end secured to the first side of the first panel along a seam between upper and lower corners of the seam, and a second end defining at least one flap securable to the second side of the first panel at a location site;
a first strap having a first end secured to the first side of the first panel and extending from an upper portion of the seam including the upper corner of the seam and overlying at least a portion of the second panel, and a second end securable to the second side of the first panel at the location site;
a second strap having a first end secured to the first side of the first panel and extending from a lower portion of the seam including the lower corner of the seam and having a second end securable to the second side of the first panel at the location site;
a dynamic force strap helically extending between upper and lower portions of the orthopedic device and connecting to the first panel; and
a hinge assembly secured to the first panel and extending between upper and lower portions of the orthopedic device, the dynamic force strap has first and second ends securing to first and second frames of the hinge assembly spaced apart by first and second struts connected to one another by a hinge.

11. The orthopedic device of claim 10, wherein the at least one flap includes first and second flaps spaced apart by a gap so that a patella opening is formed in combination with the second side of the first panel.

12. The orthopedic device of claim 11, wherein the second side of the first panel defines first and second projecting portions spaced by a notch combining with the gap to form the patella opening.

13. The orthopedic device of claim 11, wherein in an open, flat configuration, the first flap is located at least in part above the second end of the first strap, and the second flap is located at least in part above the second end of the second strap relative to the upper corner of the seam, wherein in a closed, wrapped configuration, the first flap is located below the second end of the first strap and borders the patella opening of the orthopedic device.

14. The orthopedic device of claim 13, wherein tensioning of the first and second straps is arranged independently of tensioning of the second panel via the first and second flaps.

15. The orthopedic device of claim 13, wherein when tensioning the first and second flaps to secure to the second side of the first panel, first and second edges of the second panel slope downwardly and upwardly from the upper and lower corners, respectively, toward the second side of the first panel.

16. The orthopedic device of claim 10, wherein the first strap is arranged to be secured to the second side of the first panel independently from the second strap such that the first and second straps are separated by a clearance at the seam.

17. A method for securing an orthopedic device to a leg and about a knee, the orthopedic device including a first panel defining opposed first and second sides, a second panel having a first end secured to the first side of the first panel along a seam and a first strap having a first end secured to the first side of the first panel and extending from the seam, the method comprising the steps of:
placing the orthopedic device in a flat configuration posterior of the knee and leg;
locating the seam along a posterior or a second side of the knee and leg;
wrapping the first panel from the seam about a first side of the leg and knee;
wrapping the second panel from the seam about a second side of the leg and knee;
securing a second end of the second panel to a second side of the first panel;
wrapping the first strap from the seam independently from the second panel and securing a second end to the second side of the first panel and overlying at least part of the second panel.

* * * * *